United States Patent [19]
Hodges et al.

[11] Patent Number: 5,929,307
[45] Date of Patent: Jul. 27, 1999

[54] METHOD FOR THE PRODUCTION OF HYBRID PLANTS

[75] Inventors: Thomas K. Hodges; Leszek A. Lyznik; Jeffrey Vincent; Halina Kononowicz-Hodges; Enamul Huq, all of West Lafayette, Ind.; Jang-Yong Lee, Suweon, Rep. of Korea

[73] Assignee: Purdue Research Foundation, West Lafayette, Ind.

[21] Appl. No.: 08/765,268

[22] PCT Filed: Oct. 11, 1996

[86] PCT No.: PCT/US96/16418

§ 371 Date: Dec. 20, 1996

§ 102(e) Date: Dec. 20, 1996

[87] PCT Pub. No.: WO97/13401

PCT Pub. Date: Apr. 17, 1997

Related U.S. Application Data

[60] Provisional application No. 60/005,362, Oct. 13, 1995.
[51] Int. Cl.$^6$ .............................. A01H 5/00; A01H 1/02; C12N 15/82; C12N 15/29
[52] U.S. Cl. .......................... 800/303; 800/274; 800/278; 800/287; 800/288; 800/298; 435/320.1; 435/419; 435/468; 536/23.6; 536/24.1; 536/23.72; 536/23.74
[58] Field of Search .................................. 800/274, 278, 800/287, 288, 298, 303; 435/320.1, 419, 468; 536/23.6, 24.1, 23.72, 23.74

[56] References Cited

U.S. PATENT DOCUMENTS 5,589,610  12/1996  De Beuckeleer et al. .............. 800/205

FOREIGN PATENT DOCUMENTS

WO 91/09957  7/1991  WIPO.
WO 92/13956  8/1992  WIPO.

OTHER PUBLICATIONS

Lyznik et al. Nucleic Acids Research 21(4): 969–975, 1993.
"Directed Excision of a Transgene From The Plant Genome", Russell, et al., *Mol. Gen. Genet.*, (1992), 234:49–59.
"Homologous Recombination Between Plasmid DNA Molecules in Maize Protoplasts", Lyznik, et al., *Mol. Gen. Genet.*, (1991), 230:209–218.
"The FLP Recombinase of Yeast Catalyzes Site–Specific Recombination in the Drosophila Genome", Golic and Lindquist, *Cell* vol. 59, Nov. 3, 1989, 499–509.
"Recombinase–Medicated Gene Activation and Site–Specific Integration in Mammalian Cells", O'Gorman, et al., *Science*, Mar. 15, 1991, 1351–1355, vol. 251.
"Development of a Heat Shock Inducible Expression Cassette for Plants: Characterization of Parameters for Its Use in Transient Assays", Ainley and Key, *Plant Molecular Biology*, 1990, 14:949–967.
"Gene Transfer With Subsequent Removal of the Selection Gene From The Host Gene", Dale and Ow, *Proc. Natl. Acad. Sci. USA*, vol. 88, Dec. 1991, pp. 10558–10562.
"Exchange of Gene Activity in Transgenic Plants Catalyzed by the Cre–lox Site–Specific Recombination System", Bayley, et al., *Plant Molecular Biology*, 18: 353–361, 1992.
"Maize Polyubiquitin Genes: Structure, Thermal Perturbation of Expression and Transcript Splicing, and Promoter Activity Following Transfer to Potoplasts by Electroporation", Christensen, et al., *Plant Molecular Biology*, 18: 675–689, 1992.
"A Steroid–Inducible Gene Expression System for Plant Cells", Schena, et al., *Proc. Natl. Acad. Sci. USA*, vol. 88, pp. 10421–10425, Dec. 1991.
"Site–directed recombination in the genome of transgenic tobacco", Odell et al., Mol. Gen. Gent., pp. 369–378, 1990, vol. 223.
"The Role of the loxP spacer region in P1 site–specific recombination", Hess et al., Nucleic Acids Research, vol. 14, No. 5, pp. 2289–2300, 1988.
"Transformation of Maize Cells and Regeneration of Fertile Transgenic Plants", Kamm et al., The Plant Cell, vol. 2, pp. 603–618, 1990.
"Altering the Genome by Homologous Recombination", Capecchi, Science, vol. 224, pp. 1288–1292, 1989.
"Gene Targeting in Plants", Paszkowski et al., The EMBO Journal, vol. 7, No. 13, pp. 4021–4026, 1988.
"Characterization of a Rice Pollen–Specific Gene and its Expression", Zou et al., American Journal of Botany, 81(5), pp. 552–561, 1994.
"Molecular Characterization of Rice Genes Specifically Expressed in the Anther Tapetum", Tsuchiya et al., Plant Molecular Biology, 26, pp. 1737–1746, 1994.

*Primary Examiner*—David T. Fox
*Attorney, Agent, or Firm*—Barnes & Thornburg

[57] ABSTRACT

The present invention is directed to recombinant expression vectors comprising a suicide gene flanked by site-specific recombination sequences and the use of those expression vectors to produce trangenic plants that facilitating the production of hybrid plants. The transgenic plants produced in accordance with the present invention comprise a novel male-sterility/restorer system, wherein a male sterile plant is cross-fertilized with a restorer plant to produce a hybrid plant.

24 Claims, 5 Drawing Sheets

Variety A

--lox--TAP>FRT-*suicidal gene*--FRT--inducible pro>FLP---lox---
                  any toxic gene Variety B --Ubiquitin>Cre--
any strong promoter Hybrid production conversion to sterility
spray A seedlings with chemical,
invert *suicidal* gene- A becomes male sterile.

reversion to fertility
Pollinate with B and the
F1 is (A x B) and *suicidal* is excised---fertile and cleansed of most foreign DNA Rows of Variety

Variety A

--TAP>suicidal gene--FRT--TAP>restorer gene--FRT--ln. pro>FLP--

Variety B

--Ubiquitin>restorer gene--35S>hpt--35S>gusA--

Hybrid production spray A seedlings with copper,
excise *suicidal* -- A becomes male sterile.

Pollinate with B and the
F1 is (A x B) and contains
*suicidal* and *restorer* genes Rows of Variety

METHOD FOR THE PRODUCTION OF HYBRID PLANTS

CROSS-REFERENCES TO RELATED APPLICATIONS

This application is a U.S. national phase counterpart of international application serial No. PCT/US96/16418 filed Oct. 11, 1996 which claims priority to United States provisional application Ser. No. 60/005,362 filed Oct. 13, 1995. +gi

GOVERNMENT RIGHTS

This invention was made with United States Government support under United States Department of Agriculture Grant No. 91-37301-6375. The U.S. Government has certain rights in the invention.

FIELD OF THE INVENTION

This invention relates to a method of producing hybrid plants. More particularly this invention relates to the use of novel recombinant expression vectors to produce trangenic plants comprising a novel male-sterility/restorer system that facilitates the production of hybrid plants. The system uses a site-specific recombinase to excise a male sterility.

BACKGROUND OF THE INVENTION

Hybrid plants have been demonstrated to be superior to inbred lines with respect to yield and vigor. The production of hybrid seed on a large scale is challenging because many crops have both male and female reproductive organs (stamen and pistil) on the same plant, either within a single flower or in separate flowers. This arrangement results in a high level of self pollination and makes large scale directed crosses between inbred lines difficult to accomplish.

To guarantee that outcrossing will occur during the production of hybrid seed, breeders have either manually or mechanically removed stamens from one parental line, or exploited male sterility mutations that disrupt pollen development. Manual emasculation is labor intensive and impractical for plants with small bi-sexual flowers.

Important crops like rice, corn, wheat are self-pollinating plants, and therefore there is a need to develop systems for pollination control to assist in the production of F1 hybrids. All currently available systems are based on the introduction of a male sterility trait to one parental plant followed by the introduction of a fertility-restorer gene, as a result of cross-pollination, to produce fertile hybrid plants.

Male reproductive processes in flowering plants occur in the anther. This organ is composed of several tissues and cell types, and is responsible for producing pollen grains that contain the sperm cells. A specialized anther tissue, the tapetum, plays an important role in pollen formation. The tapetum surrounds the pollen sac early in anther development, degenerates during the later stages of development and is not present as an organized tissue in the mature anther. The tapetum produces a number of proteins and other substances that either aid in pollen development or become components of the pollen outer wall. It is known that many male sterility mutations interfere with tapetum cell differentiation and/or function. Thus tapetal tissue is believed to be essential for the production of functional pollen grains.

Currently available male-sterile-based pollination systems are not satisfactory. In many cases, male sterility is unstable under different climatic conditions (Fan and Stefansson, 1986) and partial female sterility of the male-sterile plants and/or reversion to fertility of male-sterile plants has been observed. Furthermore, the restorer genes used to restore fertility to the male sterile lines have also been found to be unstable. In some cases, prominent morphological changes in the male-sterile flowers were evident (Denis et al., 1993).

Another approach to the control of fertility is based on the use of a cytoplasmic-male-sterility system. See, for example, Patterson, U.S. Pat. No. 3,861,079. However, reliance on a single cytoplasmic-male-sterile system for the production of all hybrid plants is undesirable because it leaves the entire hybrid stock vulnerable to plant pathogens. For example, extensive use of one corn cytotype, cmsT lead to an eptiphytic outbreak of Southern Corn Leaf Blight in the early 1970's. Thus, it is important to develop alternative methods to produce male sterile lines in plant species where only a single male-sterility system is available.

The present invention relates to a new method for making hybrid plants via a novel male-sterility/restorer system. The method incorporates into one plant line (line A) a male sterility system (an anther-specific promoter driving a suicidal gene) linked to a phenotypic trait (herbicide-resistance, seed coat color, seed plumpness, etc.). The phenotypic trait allows one to identify and maintain the male sterile progeny. Furthermore the male sterility system is flanked by target sites (recombination sequences) of a site-specific recombinase such that the introduction of recombinase activity excises the male sterility system, thus restoring fertility to the progeny of the male sterile plant. Plant line B is generated by incorporating a gene encoding a site-specific recombinase under the control of a constitutive (e.g. ubiquitin, CaMV35S) or cell-specific (e.g. anther, tapetum, zygote, embryo, etc.) promoter. The site-specific recombinase recognizes and interacts with the site-specific recombination sequences present in line A. After multiplication of lines A and B, the two plant lines are crossed, and expression of the site-specific recombinase in the zygote or early embryonic cells results in the recombinase enzyme excising all of the DNA between the target sites. In accordance with one embodiment the sterility system and the linked marker system are excised, giving rise to fertile plants that produce hybrid seeds.

This method can be generally applied to plants for which the pollination control systems have not yet been established, or with which the production of hybrids is not efficient. Accordingly, the present invention provides recombinant expression vectors and a method for producing the male sterile and fertility restorer plant lines utilized to produce fertile F1 hybrid plant entities.

SUMMARY OF THE INVENTION

The present invention is directed to recombinant expression vectors and the use of those vectors to develop a male sterility/restorer system for facilitating the production of hybrid plants. The system comprises two trangenic parent plants that are cross-fertilized to produce a hybrid plant entity. The first parent plant is a male sterile plant, having a DNA sequence comprising a sterility inducing gene wherein the anther-specific promoter and sterility inducing gene are flanked by a pair of site-specific recombinase sites. The second parent plant comprises a male fertility restoration plant having a DNA sequence comprising a gene encoding a site-specific recombinase that interacts with the site-specific recombinase sites present in the male sterile plant.

BRIEF DESCRIPTION OF THE DRAWINGS

FIG. 3 is a diagrammatic representation of a method for preparing a hybrid plant;

FIG. 4 is a diagrammatic representation of a method for preparing a hybrid plant.

DETAILED DESCRIPTION OF THE INVENTION

Definitions

Figure 1A:
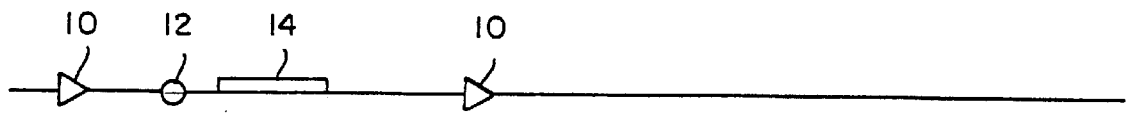
FIG. 1a, FIG. 1b, FIG. 1c and FIG. 1d are schematic representations of various DNA sequences useful for producing transgenic male sterile plants. Suicide gene (14) is operably linked to an anther-specific promoter (12). First site-specific recombination sequences (10) in conjunction with a first site-specific recombinase gene (18) operably linked to an inducible promoter (16) are utilized in one embodiment to excise the suicide gene (14) or the restorer gene (20). Second site-specific recombination sequences (22) are utilized in the construct of FIG. 1d to excise the intervening sequences.

A promoter is a DNA sequence that directs the transcription of a structural gene. Typically, a promoter is located in the 5' region of a gene, proximal to the transcription start site of a structural gene. If a promoter is an inducible promoter then the rate of transcription increases in response to an inducing agent. In contrast, the rate of transcription is not regulated by an inducing agent if the promoter is a constitutive promoter.

An anther-specific regulatory element is a DNA sequence that directs a higher level of transcription of an associated gene in anther tissue relative to the other tissues of the plant. A tapetum-specific regulatory element is a DNA sequence that directs a higher level of transcription of an associated gene in tapetal tissue relative to the other tissues of the plant. These regulatory elements can be linked to a core promoter to confer tissue specific activity to the core promoter.

An enhancer is a DNA regulatory element that can increase the efficiency of transcription, regardless of the distance or orientation of the enhancer relative to the start site of transcription.

The term expression refers to the biosynthesis of a gene product. For example, in the case of a structural gene, expression involves the transcription of the structural gene into messenger RNA and the translation of messenger RNA into one or more polypeptides.

An expression vector is a DNA molecule comprising a gene that is expressed in a host cell. Typically gene expression is placed under the control of certain regulatory elements including constitutive or inducible promoters, tissue-specific regulatory elements, and enhancer elements. Such a gene is said to be "operably linked to" the regulatory elements. Expression vector typically include eukaryotic and/or bacterial selectable markers that allow for selection of cells containing the expression vector.

An exogenous DNA sequence refers to a DNA sequence that has been introduced into a host cell from an external source. A transgenic plant is a plant having one or more plant cells that contain an exogenous DNA sequence. The term stably transformed refers to a transformed cell or plant that is capable of transmitting an exogenous DNA sequence to its progeny. Typically a stably transformed host has the exogenous DNA sequence integrated into its genome.

A ribozyme is an RNA molecule that contains a catalytic center. The term includes RNA enzymes, self-splicing RNA's, and self-cleaving RNA's. The DNA sequence that encodes a ribozyme is termed a ribozyme gene.

An external guide sequence is an RNA molecule that directs the endogenous ribozyme RNaseP, to a particular species of intracellular messenger RNA, resulting in the cleavage of the messenger RNA by RNaseP. The DNA sequence that encodes an external guide sequence is termed an external guide sequence gene.

A visible marker is defined herein as including any gene that encodes a product that produces a phenotypic trait to the host cell or organism.

The term suicide gene is used herein to define any gene that expresses a product that is fatal to the cell expressing the suicide gene.

A restorer gene is used herein to define any gene that expresses a product that interferes with the expression of the suicide gene (including products that excise the suicide gene or interfere with the transcription or translation of the gene) or interferes with the activity of the suicide gene product.

A core promoter contains the essential nucleotide sequences for promoter function, including the TATA box and start of transcription. By this definition, a core promoter may or may not have detectable activity in the absence of specific sequences that may enhance the activity or confer tissue specific activity.

A selectable marker is defined herein as including any nucleic acid sequence or gene product that can be selected for after introduction into a cell. The selectable marker facilitates the identification of transformants.

The present invention is directed to a system for generating male fertile hybrid plants. The system comprises a male sterile plant and a fertility restoring plant wherein cross-fertilization of the male sterile plant with the fertility restoring plant produces a male fertile hybrid plant.

The male sterile plants in accordance with the present invention have a DNA sequence comprising an anther-specific promoter operably linked to a sterility inducing gene, wherein at least a portion of the anther-specific promoter and the sterility inducing gene are flanked by a pair of site-specific recombination sites. The sterility of the progency of these male sterile plants can be reversed by introducing site-specific recombinase activity into the cells of the progeny plants at an early developmental stage (i.e. from zygote stage until the seedling stage of the plant). The recombinase activity can be introduced in the plant cells either by introducing a recombinase gene under the control of a constitutive promoter into the plant cell (for example by cross-pollinating the male sterile plant with a restorer plant that encodes the recombinase gene) or by inducing the expression of a recombinase gene already present in the plant cells and operably linked to an inducible promoter.

In accordance with the present invention the transgenic sterile plants and restorer plants are produced by introducing into a plant cell an expression vector that encodes the respective sterility inducing gene or restorer gene. Methods for introducing DNA constructs into plant cells are familiar to those skilled in the art. The transgenic plants produced using these methods will typically have the expression vector inserted into the genome of all, or a majority of, the plant cells of the organism. However, the expression of the suicide gene product will be limited to the specific cell type or tissue type based on the specificity of the promoter driving the expression of the gene. In accordance with one embodiment the male sterile plants comprise a suicide gene wherein the suicide gene product is expressed only in anther-specific tissues. More preferably, the gene product will be expressed only in tissues directly related to the development of pollen cells, and in one embodiment the gene product is expressed only in the tapetum cells.

In one embodiment a male sterile plant is generated by transforming plant cells with an expression vector comprising the DNA sequence as shown schematically in FIG. 1a. The expression vector comprises a suicide gene operably linked to an anther-specific promoter, wherein the sequences encoding the anther-specific promoter and suicide gene are flanked by a pair of directly repeated site-specific recombination sequences. A transgenic plant containing this expression vector will be male sterile due to the expression of the suicide gene product in the anther tissues. However the female portions of the plant remain unaffected and the male sterile plant can be fertilized by pollen from another plant to produce F1 progeny. However, unless the male sterile plant was cross-fertilized with a plant containing a restorer gene, the progeny of the cross-fertilization will also be male sterile. Thus the present system allows the propagation of male sterile plant lines, by sib-pollinating with non-restorer plants.

In one embodiment the DNA sequence shown in FIG. 1a further includes a selectable marker gene or a visible marker gene. The presence of the selectable marker gene or a visible marker gene allows the selection/identification of plant entities transformed with the expression vector. Thus the selectable marker gene/visible marker gene can be utilized to confirm the presence of the suicide gene and the sterility of the progeny plants.

Advantageously fertile F1 hybrids can be generated by cross-fertilizing a male sterile plant comprising the DNA sequence of FIG. 1a with a plant containing a restorer gene. In one embodiment the restorer plant comprises a DNA sequence encoding a site-specific recombinase gene wherein the expressed site-specific recombinase interacts with the site-specific recombination sequences flanking the suicide gene resulting in excision of the suicide gene from the genome of the F1 hybrid plants. In accordance with this embodiment, the site-specific recombinase gene is operably linked to a constitutive promoter or a tissue specific promoter.

The suicide gene used in accordance with the present invention encodes a protein capable of disrupting the production of functional pollen cells. Proteins capable of disrupting anther cell function include proteins that inhibit the synthesis of macromolecules that are essential for cellular function, enzymes that degrade macromolecules that are essential for cellular function, proteins that alter the biosynthesis or metabolic metabolism of plant hormones and proteins that inhibit a specific function or development of anther/tapetum cells. For example, Mariani et al., Nature, 347:737, (1990), have shown that expression of either *Aspergillus oryzae* RNase-TI or an RNase of *Bacillus amyloliquefaciens*, designated "barnase", in the tapetal cells of a plant induced destruction of the tapetal cells, resulting in male infertility. Other genes can be used as alternatives to barnase for the development of male sterile plants, such as an anther-specific β-1,3-glucanase (Hird et al. The Plant Journal 4:1023–1033, 1993), or the male sterility gene described by Aarts et al. Nature 363: 715–717, 1993.

Alternatively male sterility can be induced by the expression of an antisense RNA. The binding of an antisense messenger RNA molecule to target messenger RNA (mRNA) molecules results in hybridization arrest of translation. Thus, a suitable antisense molecule would have a sequence that is complimentary to that of a messenger RNA species encoding a protein that is essential for tapetal cell function or pollen synthesis. Typically the antisence gene would be operably linked to an anther-specific promoter to limit the expression of the antisence RNA to cells relevant to pollen production. In one embodiment an expression vector is prepared, using techniques known to those skilled in the art, that expresses an antisense RNA that interferes with the expression of the RTS2 (SEQ ID NO: 1) gene product. Alternatively, the antisense of PRK1 (pollen-expressed receptor-like kinase) from *Petunia inflata* (Mu et al. The Plant Cell 6:709–721, 1994), or the antisense of the Bcp1 male fertility gene of Arabidopsis (Xu et al. Proc. Natl. Acad. Sci. 92: 2106–2110, 1995) can be utilized as an antisense suicide gene.

The suicide gene may also encode a ribozyme. Ribozymes can be designed to express endonuclease activity that is directed to a certain target sequence in a messenger RNA molecule. For example, Steinecke et al., EMBO J., 11:1525, (1992), achieved up to 100% inhibition of neomycin phosphotransferase gene expression by ribozymes in tobacco protoplasts. The suicide gene may also encode an RNA molecule capable of promoting RNaseP-mediated cleavage of target messenger RNA molecules. According to this approach an external guide sequence can be constructed for directing the endogenous ribozyme, RNaseP, to a particular species of intracellular messenger RNA which is subsequently cleaved by the cellular ribosome. See Altman et al., U.S. Pat. No. 5,168,053 and Yuan et al., Science, 263:1269, (1994).

Anther-specific promoters and genes are known in the art. See, for example McCormick et al. "anther-specific genes: molecular characterization and promoter analysis in transgenic plants"; in Plant Reproduction: From Floral Induction to Pollination, Lord et al. (Editor), pages 128–135, (1989); and Scott et al., The Plant Cell 4: 253, (1992). However, there are no generally accepted consensus sequences that confer anther-specific gene expression. Consequently, it is not possible to isolate an anther-specific regulatory element directly from a plant genomic library by screening for a consensus sequence. In accordance with the present invention these anther specific promoters can be operably linked to a suicide gene and flanked by site-specific recombinase sequences for use in producing male sterile plants. In one embodiment a tapetum specific promoter is used to drive the expression of the suicide gene and in particular, one tapetum specific promoter useful in the present invention is the tapetum specific promoter of SEQ ID NO: 2.

The suicide gene of the DNA constructs used to produce male sterile lines is flanked with site-specific recombination sites to enable the removal of the suicide gene through the use of a site-specific recombinase system. In general, a site-specific recombinase system consists of two elements: a pair of DNA sequences (the site-specific recombination sequences) and a specific enzyme (the site-specific recombinase). The site-specific recombinase will catalyze a recombination reaction only between two site-specific recombination sequences.

Depending on the orientation of the site-specific recombination sequences, intervening sequences will either be excised or inverted in the presence of the site-specific recombinase. When the site-specific recombination sequences are orientated in opposite directions relative to one another (ie, inverted repeats) then any intervening sequences will be inverted relative to the other sequences in the genome. Therefore, if inverted repeats of the site-specific recombination sequences are present at both ends of DNA introduced into the cell, the sequence located between the two repeats can be subsequently inverted (rotated 180°) by interaction of the site-specific recombination sequences with their site-specific recombinase. However, if the site-specific recombination sequences are orientated in the same direction relative to one another (ie, direct repeats) any intervening sequences will be deleted upon interaction with the site-specific recombinase.

A number of different site-specific recombinase systems can be utilized in accordance with the present invention, including but not limited to the Cre/lox system of bacteriophage P1, the FLP/FRT system of yeast, the Gin recombinase of phage Mu, the Pin recombinase of E. coli, and the R/RS system of the pSR1 plasmid. The two preferred site-specific recombinase systems are the bacteriophage P1 Cre/lox and the yeast FLP/FRT systems. In these systems a recombinase (Cre or FLP) interacts specifically with its respective site-specific recombination sequence (lox or FRT respectively) to invert or excise the intervening sequences. The sequence for each of these two systems is relatively short (34 bp for lox and 34–47 bp for FRT). Site-specific recombinase systems are described in U.S. Pat. No. 5,527,695, the disclosure of which is expressly incorporated herein.

The suicide gene can be flanked by direct repeats of the site-specific recombination site, and subsequent introduction of recombinase activity excises the suicide gene and thus restores fertility. Alternatively, by placing either the suicide gene's promoter or at least a portion of the coding region of the suicide gene between indirect repeats of a site-specific recombinase system, subsequent introduction of the site-specific recombinase will invert the sequence thus inactivating the gene. The recombination reaction is reversible and the intervening sequences can be inverted a second time to restore function to the gene allowing expression of its product.

The FLP/FRT recombinase system has been demonstrated to function efficiently in plant cells. Experiments on the performance of the FLP/FRT system in both maize and rice protoplasts indicates that FRT site structure, and amount of the FLP protein present, affects recombinase activity. In general, short incomplete FRT sites lead to a higher frequency of excision events than the complete full-length FRT sites. The recombination reaction is reversible, however altering the structure of the site-specific recombination sequences can alter the reversibility of the reaction. The site-specific recombination sequence can be mutated in a manner that the product of the recombination reaction is no longer recognized as a substrate for the reverse reaction, thereby stabilizing the inversion or excision event.

Although the site-specific recombination sequences must be linked to the ends of the DNA sequence to be inverted, the gene encoding the site-specific recombinase may be located elsewhere. For example, the recombinase gene can be directly introduced into cells through standard transformation procedures, or through cross-pollination with a plant that already contains the recombinase gene. Alternatively, the recombinase gene could already be present in the plant's DNA and operably linked to an inducible promoter.

Inducible promoters include any promoter capable of increasing the amount of gene product produced, by a given gene, in response to exposure to an inducer. Inducible promoters are known to those familiar with the art and a variety exist that could conceivably be used to drive expression of the recombinase gene. Inducible promoters suitable for use in accordance with the present invention include the heat shock promoter, the glucocorticoid system and any chemically-inducible promoter, including tetracycline, Cu-, etc. Promoters regulated by heat shock, such as the promoter normally associated with the gene encoding the 70-kDa heat shock protein, can increase expression several-fold after exposure to elevated temperatures. The heat shock promoter can be used as an environmentally inducible promoter for controlling transcription of the recombinase gene. The glucocorticoid system also functions well in triggering the expression of genes. The system consists of a gene encoding glucocorticoid receptor protein (GR) which in the presence of a steroid hormone forms a complex with the hormone. This complex then binds to a short nucleotide sequence (26 bp) named the glucocorticoid response element (GRE), and this binding activates the expression of linked genes. The glucocorticoid inducible promoter system has been shown to function in transgenic tobacco (Mett et al. 1993) and can also be used to control the expression of a site-specific recombinase gene.

Figure 1B:
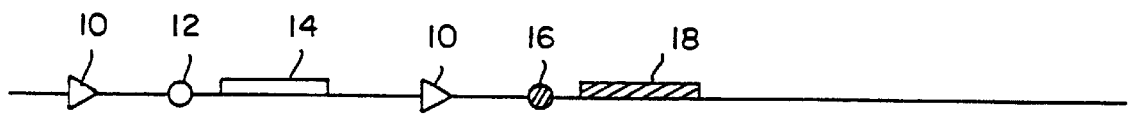

In accordance with one embodiment the male sterility plant is produced by transforming plant cells with an expression vector comprising the DNA sequence as shown schematically in FIG. 1B. The sequence comprises a suicide gene operably linked to an anther-specific promoter and a gene expressing a site-specific recombinase that specifically interacts with the site-specific recombination sites. The site-specific recombinase gene is operably linked to an inducible promoter. The sequences encoding the anther-specific promoter and suicide gene are flanked by a pair of directly repeated site-specific recombinase sequences. Furthermore the construct may include a selectable marker or visible marker gene. In an alternative embodiment of this expression vector the DNA sequences encoding the site-specific recombinase gene are also located between the directly repeated site-specific recombination sequences, resulting in self-excision.

Figure 1C:
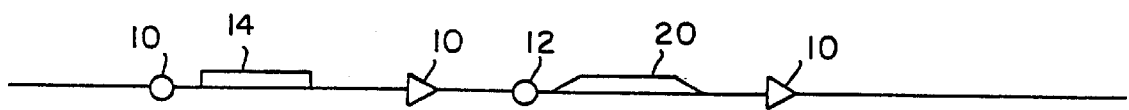

In another embodiment a male sterile plant is generated by transforming plant cells with an expression vector comprising the DNA sequence as shown schematically in FIG. 1C. The sequence comprises a suicide gene, a restorer gene, a pair of directly repeated site-specific recombinase sites flanking the DNA sequence encoding the restorer gene wherein the expression of the suicide gene and the restorer gene are controlled by an anther-specific regulatory element. Advantageously, a plant transformed with this expression vector is not initially male sterile. This allows the initially transformed plant to be self-pollinated to produce a large number of progeny. Male sterility can be induced in any of these plants upon the introduction of site-specific recombinase activity into the plant cells. The site-specific recombinase activity results in the removal of the restorer gene thus resulting in an active suicide gene product which induces male sterility. Fertile hybrid plants can then be generated from this male sterile plant by cross-fertilizing the male sterile plant with a plant containing the restorer gene expressed under a constitutive promoter or an anther-specific promoter.

Figure 1D:
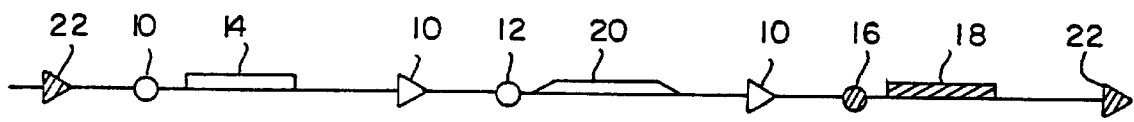

A second site-specific recombination system can be added to the expression vector of FIG. 1C to produce an expression vector as shown schematically in FIG. 1D. This expression vector comprises a multi-functional DNA sequence encoding a suicide gene and a restorer gene wherein the expression of the suicide gene and the restorer gene are controlled by an anther-specific regulatory elements. The expression vector further comprises a pair of first site-specific recombination sites flanking the DNA sequences encoding the restorer gene and a gene encoding a first site-specific recombinase operably linked to an inducible promoter. The expression vector further comprises a pair of directly repeated second site-specific recombinase sites that flank the multi-functional DNA sequence.

A plant cell transformed with expression vector 1D will not be male sterile. However upon induction to the inducible promoter of the first site-specific recombinase the restorer gene will be removed from the plant's genome resulting in a male sterile plant. A fertile hybrid plant can then be generated by crossing the male sterile plant to a plant having a DNA sequence that expresses a second site-specific recombinase that interacts with the second site-specific recombination sites on expression vector 1D which results in the removal of the suicide gene.

Transformation

Through the use of recombinant DNA technology, foreign DNA sequences can be inserted into an organism's genome to alter the phenotype of the organism. These gene sequences will typically be present in all cells. However, expression of the gene's product may be limited to a specific cell type or tissue type based on the specificity of the promoter driving the expression of the gene. In accordance with one embodiment of the present invention, plant cells are transformed with DNA sequences under the control of a promoter that expresses the DNA sequences only in anther-specific tissues. More preferably, the gene product is expressed only in tissues directly related to the development of pollen cells, more preferably the tapetum cells. In accordance with one embodiment of the present invention the plant is transformed with a suicide gene (operably linking to an anther-specific promoter) that expresses a protein product that is cytotoxic to plant cells, or interferes with normal pollen development (i.e. the use of anti-sense mRNA). The selection of the suicide gene is not critical provided that the gene product is toxic to plant cells. Suitable genes for expressing plant cell cytotoxic products are known to those skilled in the art.

The DNA constructs of the present invention can be constructed using recombinant DNA technology known to those skilled in the art. The recombinant gene constructs can be inserted into commercially available expression vectors to express the gene product in the transformed cells.

The creation of a transformed cell requires that the DNA be physically placed within the host cell. The DNA can be introduced into cells using a variety of techniques known to those skilled in the art. For example, in one form of transformation, the DNA is microinjected directly into cells though the use of micropipettes. Alternatively, high velocity ballistics can be used to propel small DNA associated particles into the cell. In another form, the cell is permeablized by the presence of polyethylene glycol, thus allowing DNA to enter the cell through diffusion. DNA can also be introduced into a cell by preparing protoplasts and fusing the prepared protoplasts with other entities which contain DNA. These entities include minicells, cells, lysosomes, other protoplasts or other fusible lipid-surfaced bodies. Electroporation is also an accepted method for introducing DNA into a cell. In this technique, cells are subject to electrical impulses of high field strength which reversibly permeabilizes biomembranes, allowing the entry of exogenous DNA sequences.

In addition to these "direct" transformation techniques, transformation can be performed via bacterial infection using *Agrobacterium tumefaciens* or *Agrobacterium rhizogenes*. This system is particularly useful for transforming plant cells. The Agrobacterium bacterial strains contain a plasmid (called Ti or Ri respectively) one portion of which, named transferred DNA (T-DNA) is transmitted into plant cells after infection by Agrobacterium and integrated into the genomic DNA of the plant cell. This system has been extensively described in the literature and can be modified to introduce foreign genes and other DNA sequences into plant cells.

Transformed cells (those containing the DNA inserted into the host cell's DNA) are selected from untransformed cells through the use of a selectable marker included as part of the introduced DNA sequences. Transformed cells/plant entities can also be identified by the expression of a visible marker included as part of the introduced DNA sequences. Visible markers include genes that impart a visible phenotypic trait such as seed color (i.e. yellow, purple or white genes) or shape (i.e. shrunken or plump genes). Selectable markers include genes that provide antibiotic resistance or herbicide resistance. Cells containing selectable marker genes are capable of surviving in the presence of antibiotic or herbicide concentrations that kill untransformed cells. Examples of selectable marker genes include the bar gene which provides resistance to the herbicide Basta, the nptII gene which confers kanamycin resistance and the hpt gene which confers hygromycin resistance. An entire plant can be generated from a single transformed plant cell through cell culturing techniques known to those skilled in the art.

Hybrid Plant Production

In accordance with one embodiment, a male sterile line for use in hybrid plant production can be generated, using techniques known to those skilled in the art, from a fertile plant variety A by transforming plant cells with a sterility inducing DNA construct to produce a sterile variety A(t). The sterility inducing DNA construct comprises an anther-specific (tapetum-specific) promoter operably linked to a suicide gene, a marker gene (for example a visible marker gene that effects seed color or shape or a selectable marker gene such as a herbicide resistant gene) and a pair of directly repeated site-specific recombination sequence (for example the FRT recombination sequences of the FLP/FRT recombinase system). (See FIG. 2). The marker gene and the suicide gene are flanked by direct repeats of the site-specific recombination sequences.

Plant cells transformed with this DNA construct are identified based on the presence of the marker gene. In one embodiment the marker gene is a selectable marker, for example, the bar gene operably linked to the cauliflower mosaic virus 35S promoter. The bar gene encodes a product resistant to the herbicide Basta.

Figure 2:
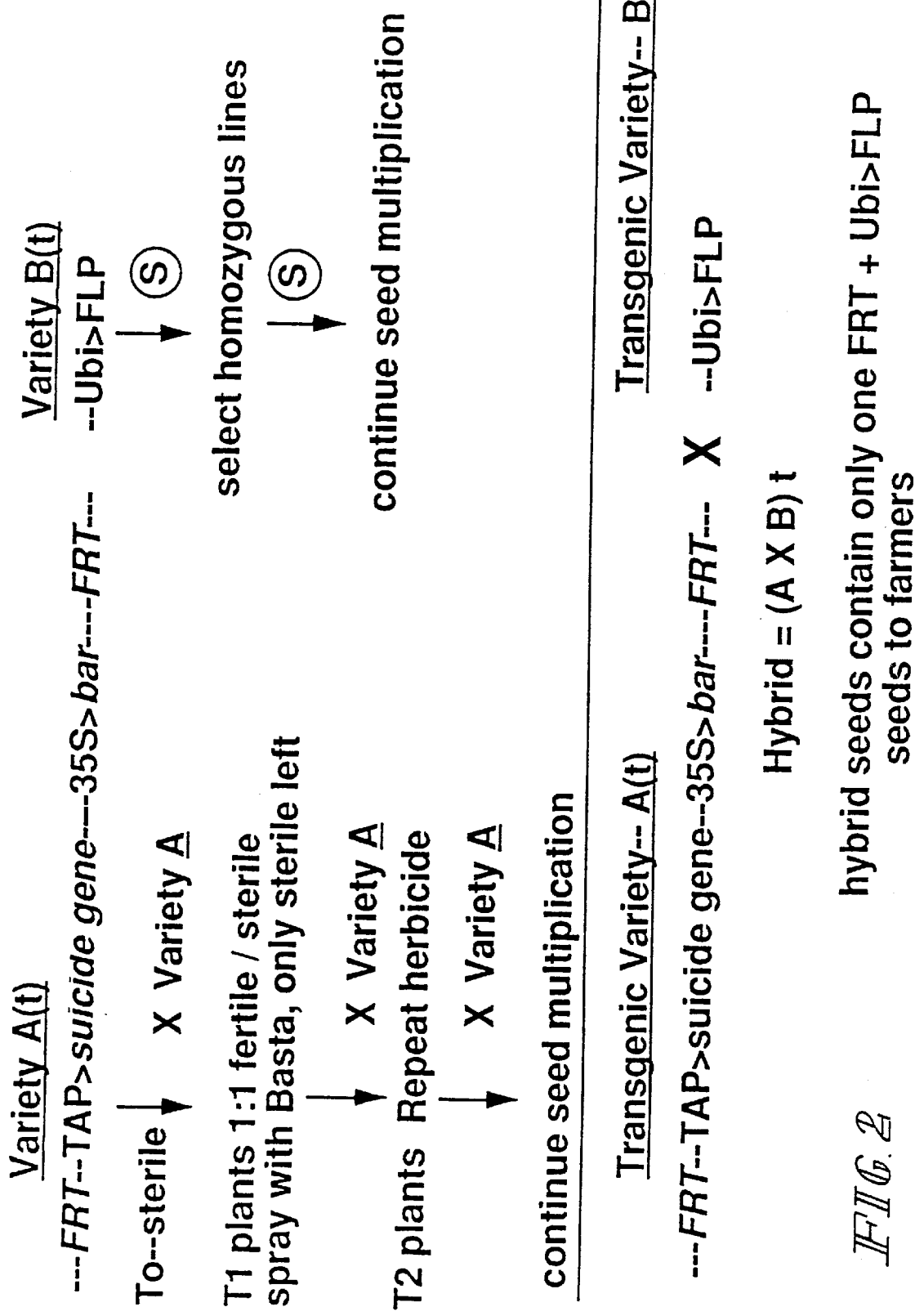
FIG. 2 is a diagrammatic representation of a method for preparing a hybrid plant.

Plants containing the DNA construct shown in FIG. 2 are male sterile as a result of the suicide gene product being expressed in the tapetum cells. The male sterile transgeneic variety A(t) can be maintained by pollinating the A(t) variety with pollen from the original variety A plants. The progeny can then be screened by spraying with the herbicide Basta and only those plants retaining the DNA construct survive. Those plants retaining the DNA construct are male sterile. Assuming a single locus of the DNA construct is present in the transgenic variety A(t), crossing the A(t) with variety A should produce a 1:1 male fertile to male sterile ratio. The male sterile lines can be repeatedly crossed with variety A to produce a large number of male sterile seeds for use in the production of a hybrid.

The direct repeats of the site-specific recombination sequences present in the sterility inducing DNA construct allow subsequent removal of the suicide gene and restoration of fertility upon introduction of site-specific recombinase activity to the cells. Accordingly, in one embodiment transgenic variety A(t) can be crossed with a male fertility restoring variety B(t) to produce the desired hybrid. Restorer plant variety B(t) is produced from variety B by transforming variety B with a DNA construct comprising a recombinase gene (for example the FLP recombinase gene of the FLP/FRT recombinase system) operably linked to a constitutive promoter. Transgenic variety B(t) can then be crossed with transgenic variety A(t) to produce a fertile hybrid strain. Expression of the recombinase gene in the hybrid strain results in the excision of the DNA sequences (encoding the suicide gene) located between the site-specific recombination sequences that originated from parental variety A(t). Therefore the hybrid seeds contain only one site-specific recombination sequence and the recombinase gene. The plants produced from the hybrid seed will be fertile.

In an alternative embodiment male sterile plants can be produced through the use of the sterility inducing DNA construct shown in FIG. 3. In accordance with this embodiment plant variety A is transformed with a sterility inducing DNA construct comprising a multifunctional sequence comprising a suicide gene flanked by a pair of inverted repeats of a first site-specific recombination sequence (for example the FRT recombination sequence of the FLP/FRT recombinase system). The suicide gene is located adjacent to a tapetum-specific promoter (the promoter being located outside the sequences flanked by the first site-specific recombination sequences) but is inverted relative to the promoter such that the suicide gene is not transcribed. The multifunctional sequence further comprises an inducible promoter operably linked to a first site-specific recombinase gene (for example the FLP recombinase gene of the FLP/FRT recombinase system) and the multifunctional sequence is flanked by a pair of directly repeated second site-specific recombination sequence (for example the lox recombination sequence of the cre/lox recombinase system).

A plant transformed with this DNA construct will be fertile (thus facilitating seed production), however upon induction of the inducible promoter, first site-specific recombinase activity will be introduced into the cell and the recombinase will interact with the first site-specific recombination sequences to invert the suicide gene. Inversion of the suicide gene operably links the tapetum-specific promoter to the suicide gene resulting in expression of the suicide gene product and male sterility in the plant. The sterility inducing DNA construct can further include a visible marker gene or selectable marker gene to allow identification of plants having the sterility inducing DNA construct.

As shown in FIG. 3, the direct repeats of the second site-specific recombination sequences present in the sterility inducing DNA construct allow subsequent removal of the multifunctional DNA sequence and restoration of fertility upon introduction of second site-specific recombinase activity to the cells (for example the cre recombinase gene of the cre/lox recombinase system). Accordingly, male sterile variety A can be crossed with a male fertility restoring variety B to produce the desired male fertile hybrid.

In another embodiment male sterile plants can be produced through the use of the sterility inducing DNA construct of FIG. 4. In accordance with this embodiment plant variety A is transformed with a sterility inducing DNA construct comprising a multifunctional sequence comprising a suicide gene operably linked to a tapetum-specific promoter, a restorer gene operably linked to a tapetum-specific promoter, wherein the restorer gene is flanked by a pair of directly repeated site-specific recombination sequence (for example the FRT recombination sequence of the FLP/FRT recombinase system) and a site-specific recombinase gene (for example the FLP recombinase gene of the FLP/FRT recombinase system) operably linked to an inducible promoter. In one embodiment the restorer gene comprises an anti-sense gene that interferes with the expression of the suicide gene.

A plant transformed with this DNA construct will be fertile since the restorer gene (for example Barstar gene product) will interact with the suicide gene (for example Barnase gene product) to negate the effect of the suicide gene. However upon induction of the inducible promoter, site-specific recombinase activity will be introduced into the cell, the recombinase will interact with the site-specific recombination sequences flanking the restorer gene to excise the restorer gene. After excision of the restorer gene, the suicide gene will be expressed and will be active resulting in male sterility. The sterility inducing DNA construct can further include a visible marker or gene or selectable marker gene to allow identification of plants having the sterility inducing DNA construct.

In another embodiment a construct similar to that shown in FIG. 4 is utilized to generate male sterile plants. The only difference being related to the position and orientation of the site-specific recombination sequences. In this embodiment the restorer gene is flanked by a pair of inverted repeats of a site-specific recombination sequences. Furthermore, the tapetum-specific promoter driving the expression of the restorer gene is positioned outside the sequences flanked by the inverted repeats of the site-specific recombination sequences. Plants transformed with this construct are male fertile since the restorer gene product negates the suicide gene product. However introduction of recombinase activity inverts the restorer gene preventing expression of the restorer gene and leading to male sterility.

As shown in FIG. 4, the male sterile plant can be cross-pollinated with a plant variety containing a restorer gene and a selectable marker. Selection of progeny plants having the selectable marker will be male fertile.

EXAMPLE 1

Transformation of Rice Cells

*Agrobacterium tumefaciens* strain, LBA 4404, harboring the binary vector pTOK233 which contains the virB, virC, and virg genes from Ti-plasmid pTiBo542 [as described in Hiei et al. The Plant Journal 6:271–282 (1994)], and within the T-DNA, the npt, hpt, and intron-gusA genes. LBA 4404 (pTOK233) was tested for its potential to produce stably transformed rice callus and plants. Japonica and indica varieties of rice were transformed. Young embryos were co-cultivated with LBA 4404 (pTOK233) for 3 days in the dark at 26° C. and grown for three weeks in 250 mg/l carbenicillin and 100 mg/l cefotaxime. The resulting calli were cut into 1–2 mm sizes and plated for selection with antibiotics (three weeks in 250 mg/l carbenicillin, 100 mg/l cefotaxime and 30 mg/l hygromycin). Plants were then regenerated from the selected calli and grown as putative transgenic plants.

The efficiencies for producing transgenic plants using Agrobacterium-mediated transformation of different varieties of rice are shown in Table 1 (Y.E.=young embryos; G$^+$=Gus positive). For Radon, a japonica variety, the efficiency [see column labeled—No. of Y.E. with G$^+$ plants/ embryo plated(%)] averaged about 27%, i.e. 27% of the initial embryos treated yielded transformed plants based upon resistance to hygromycin and expression of GUS activity. Transformation of the putative transformants was confirmed by Southern analysis. All confirmed transformants obtained to date have been fertile with seed-set being nearly equivalent to that obtained from seed-grown plants.

As in the case of Agrobacterium-mediated transformation of dicots, the transgene integration pattern into the rice genome is presumably random, but the number of copies inserted and the frequencies of gene rearrangements are less than that observed by direct DNA uptake methods. Preliminary segregation studies follow a 3:1 segregation ratio for GUS indicating Mendelian inheritance of a single gene.

These latter results also eliminate the possibility of Agrobacterium contaminants (or inhabitants) being responsible for the results.

TABLE 1

| Variety | Expt. no. | No. of young embryos plated (A) | No. of young embryos with calli | No. of calli plated | No. of calli selected | No. of calli foreign | No. Y.E. with G calli (B) | % eff. (B/A) | No. Y.E. with G plants/ embryo plated (%) |
|---------|-----------|---------------------------------|---------------------------------|---------------------|-----------------------|----------------------|---------------------------|--------------|-------------------------------------------|
| Radon   | 1         | 62                              | 42                              | 352                 | 102                   | 45                   | 20                        | 32.25        | 18/62 (29.0)                              |
|         | 2         | 70                              | 62                              | 363                 | 189                   | 101                  | 43                        | 61.40        | 24/70 (34.3)                              |
|         | 3         | 75                              | 53                              | 387                 | 113                   | 68                   | 24                        | 32.00        | 22/75 (29.3)                              |
|         | 4         | 35                              | 34                              | 300                 | 161                   | 104                  | 14                        | 40.00        | 7/35 (20.0)                               |
|         | 5         | 28                              | 14                              | 86                  | 28                    | 13                   | 7                         | 25.00        | 2/28 (7.1)                                |
| TSC10   | 1         | 203                             | 119                             | 987                 | 161                   | 15                   | 13                        | 6.00         | 1/203 (0.5)                               |
|         | 2         | 84                              | 63                              | 384                 | 135                   | 98                   | 5                         | 5.90         | 1/84 (1.6)                                |
| IR72    | 1         | 60                              | 48                              | 232                 | 70                    | 52                   | 4                         | 6.60         | 5/60 (8.3)                                |
|         | 2         | 105                             | 53                              | 257                 | 93                    | 51                   | 9                         | 8.50         | 2/105 (1.9)                               |

EXAMPLE 2
Isolation of a Promoter/Gene From Rice that is Functional During Early Stages of Pollen Development:

The present invention provides a substantially pure nucleic acid sequence that encodes a tapetum-specific gene as set forth in SEQ ID NO: 1. In addition, the tapetum-specific promoter of that gene is provided as set forth in SEQ ID NO: 2. That gene (clone RST2 was isolated from rice in accordance with the following method.

A cDNA library of poly(A⁺)RNA from the panicle of IR54 rice was prepared. Panicles were harvested at the stage when the distance between leaf auricles of the first and second leaves was zero, i.e. they were at the same position. This stage is generally acknowledged as the most vigorous meiotic stage of the pollen mother cell. This cDNA library was differentially screened against leaf and panicle cDNAs, and 38 putative panicle-specific cDNA clones were obtained. Among these 38, 36 were further screened for anther-specificity by using cDNA probes from different parts of the panicle, i.e. rachis, upper half of spikelet and lower half of spikelet (anthers are located in the lower part of the spikelet during the developmental stage the samples were harvested). By using different stringencies of washing two clones were selected as possible candidates for further testing for their tissue-specificity. Total RNA was isolated from rice leaves, immature seeds, and from panicles taken at the same stage of development as that from which the cDNA clones were developed and at earlier and later stages of panicle development. These RNA species were hybridized with the two possible tapetum specific cDNA clones and analysis of the Northern blots indicated that the gene was specifically expressed in the panicle and developmentally regulated. In situ hybridizations with cDNA clone RTS1 as the probe produced a strong hybridization signal in the tapetum, the innermost layer of the anther wall surrounding the meiotic sporogenous cells in the anther. Treatment of the in situ tissue on the slides with RNase A before BSA coating resulted in the complete loss of hybridization of the probe to the tissue. Leaves did not show hybridization above background levels.

An EcoRI/XhoI fragment (0.6 kb) of the RTS1 cDNA clone was used as a probe for screening an IR54 genomic library, and three positive genomic DNA clones were obtained. These clones were mapped with restriction enzymes, and a 4.3 kb SacI/HindIII fragment (RTS2) that hybridized to the RTS1 cDNA probe was subcloned into the vector pGEM-3Zf(−). The cloned cDNA (RTS1) and the corresponding genomic clone (RTS2) including 1.2 kb nucleotide upstream of the translation start site have been sequenced. See SEQ ID No: 1 and SEQ ID No: 2 for the sequence of the promoter of the tapetum-specific RTS2 gene (SEQ ID NO:2) and the entire RTS2 gene (SEQ ID NO:1).

Sequence comparison between the cDNA clone and the genomic clone indicated that this gene has no introns and a continuous 285 base pair open reading frame encoding 94 amino acids (8.62 Kd). From a primer extension experiment, two primer extension products were identified which are separated by one nucleotide (map positions 76 and 78 upstream of the putative ATG translation initiation codon). These primer extension products were identified only when panicle RNA was used and not with leaf RNA. A TATA box sequence is present 33 nucleotides upstream of the first putative transcription start site. The 5' untranslated sequence contains one poly (dA) region, which contributes to the leader sequence with a relatively high (44.9%, 35 out of 78) deoxyadenylate content. A polyadenylation signal sequence (AATAAA) is present at 37 nucleotide downstream of the putative translation stop codon, and the predicted length of the 3' untranslated region is 208 nucleotides long.

A search of existing data bases performed by NCBI using the BLAST network service showed no significant similarity between the coding region of this gene and other genes—either for the nucleotide sequence or the deduced amino acid sequence.

Southern analyses indicated the RTS2 gene is present in variety IR54 as a single copy gene and is present in two copies in the following rice varieties: indica varieties IR52 and IR57, two japonica varieties (Calrose and Milyang #15), one indica x japonica variety (Milyang #23), but no copies were detected in tobacco (cv. Wisconsin).

EXAMPLE 3
Recombination in Maize Cells

The FLP/FRT system of yeast and the Cre/lox system of bacteriophage P1 are the primary candidates for applications in genetic studies of higher eukaryotes. They represent a simple two-component (recombinase and its target site) recombination system which does not discriminate between the integrative and excisional recombination activities. The Cre recombinase has been successfully used to activate, or inactivate, genes that had been integrated into genomic DNA of plant cells or mouse cells. Seed-specific gene activation mediated by the Cre/lox system has also been demonstrated in transgenic tobacco. The following experiment was conducted to investigate whether genomic recombinations can be induced in maize cells by the yeast FLP/FRT site-specific recombination system.

Materials and Methods
Plasmid Constructions and Transformation Procedure.

Construction of the pUbiFLP vector was described in U.S. Pat. No. 5,527,695, the disclosure of which is expressly incorporated herein. The vector pUFNeoFmG, containing a neo gene bordered by a full-length and a modified the FRT site and the promoterless gusA gene (a recombination marker), was constructed from pUFRTG by replacement of the gusA coding sequence (the SmaI-SacI fragment) with the neo coding sequence (BamHI fragment of pTO77) to give pUFRTNeo vector. The BamHI-EcoRI fragment of pU2FRTmG comprising a promoterless gusA gene, the first intron of maize Ubi-1 gene, and a modified FRT site was subsequently blunt-end ligated into the EcoRI site of the pUFRTNeo vector to form pUFNeoFmG.

The detailed description of procedures used for maize Al88xBMS protoplast isolation, transformation, culture, and selection are familiar to those skilled in the art and are described in detail in the Maize Handbook, eds. Freeling and Walbot (Sprnger-Verlag, New York), pp. 603–609. Briefly, $1 \times 10^7$ protoplasts in 1 ml of transformation medium [100 mM MES (pH 5.5), 0.2 M mannitol, 80 mM $CaCl_2$] were mixed with 50 µl of plasmid DNA (1 mg/ml) and 1 ml of 50% PEG (MW=8,000; Sigma Chemical Co., St. Louis, Mo.) in F-solution. After 30 min incubation at room temperature followed by PEG dilution and protoplast washing in protoplast culture medium, transformed protoplasts (0.2 ml of protoplast suspension at $1 \times 10^6$ viable protoplasts per 1 ml) were plated onto Millipore filters (0.8 gm pore size) that overlay feeder cells. One week later, the Millipore filters were transferred onto fresh feeder plates containing 100 µg/ml kanamycin sulfate for selection of transgenic calli. After one week, the microcalli were transferred onto Murashige and Skoog medium containing 2 mg/L 2,4-dichlorophenoxyacetic acid supplemented with 100 µg/ml kanamycin sulfate for further selection.

Southern Blot Analysis, PCR, and DNA Sequencing.

Genomic DNA was isolated from callus tissue by grinding about 500 mg of tissue in 5 ml of DNA extraction buffer. After 15 min incubation at 60° C., an equal volume of phenol was added, and the homogenate was centrifuged to separate aqueous and organic layers. DNA was precipitated from the aqueous phase by adding an equal volume of isopropanol, and after centrifugation, the DNA pellet was dissolved in TE buffer. Subsequent steps of CsCl density gradient centrifugation were performed. Genomic DNA (5 µg) was digested and electrophoresed in a 0.8% agarose gel. Southern, blot analysis was performed using vacuum transfer to Hybond-N membrane (Arnersham., Arlington Heights, Ill.), UV membrane irradiation, and hybridization to the radioactive gusA coding sequence probe according to standard procedures. PCR analysis for detection of the recombination products was performed using the primers corresponding to the 3' end of the ubiquitin promoter (5'-CCCCAACCTCGTGTTG-3', SEQ ID NO:3) and to the end of the gusA coding sequence (5'-CGCGATCCAGACTGAATGC-3', SEQ ID NO:4). The length of the amplified fragment should be 1.2 kb and 2.8 kb for the product and substrate of the recombination reaction, respectively. One hundred to 200 mg of DNA was subjected to 30 cycles of amplification of three steps each (94° C., 1 min, 60° C., 1 min, 72° C., 2 min) in PCR buffer (10 mM Tris-HCI, pH 8.4-, 50 mM KCl; 1.5 mM $MgCl_2$; 0.01% gelatin, Perkin-Elmer) containing 0.2 mM of each dNTP, 0.1 nM of each primer, and 1.25 units of native Taq DNA polymerase (Perkin-Elmer, Norwalk, Conn.). PCR products were analyzed by gel electrophoresis in 1.0% agarose gels.

For DNA sequencing, the 1.2 kb PCR amplified fragment was phosphorylated with T4 DNA kinase (New England BioLabs, Beverly, Mass.) and was then blunt-end ligated into the SmaI site of the pGEM7Zf(+) vector (Prome-ga, Madison, Wis.).

GUS and NPTII activity assays

Samples of transgenic, calli were sonicated for 5–10 sec in GUS extraction buffer containing 0.1% Triton X-100. After centrifugation for 5 min at 16,000×g, the supernatant was used directly for GUS activity and protein assays. GUS activity was assayed using a fluorogenic substrate (MUG; 4-methyl-umberiferyl b-D-glucuronide) and a Perkin Elmer LS50B fluorometer. Reactions were terminated at timed intervals, and GUS activity was calculated from the slope of the line generated from time points and normalized to the protein content. NPTII activity was assayed using the dot-blot method. Callus extracts (prepared as for the GUS activity assay) were incubated in a reaction buffer containing 335 mM Tris-HCI (pH7.1), 210 mM $MgCl_2$, 2 M $NH_4CI$, 0.001 mM ATP. 0.03 mM neomycin, 10 mM NaF, 1 to 2 mCi/ml $^{32}$P-ATP. Aliquots of the reaction mixture were blotted onto Whatman P81 paper. The blot was washed with 10 MM phosphate buffer (pH 7.5), dried, and washed again with the same buffer at 80° C. for 10–15 min. The P81 paper was exposed to X-ray film for one to several hrs (exposure time depended an NPTII activity) at room temperature.

Integration of Recombination Test Vector into Maize Genomic DNA.

The vector, pUFNeoFmG, was used to assay the FLP activity in maize cells. It provides a fully functional neo gene to select stably transformed cells and a promoterless gusA gene whose subsequent activation should indicate an FLP-mediated excision of the neo gene. Excision of the neo gene operably links the ubi promoter to the gusA gene resulting in gusA expression. The two FRT sites flanking the neo gene were different. The modified FRT site (FRTm) contained only two symmetry elements. As discussed later, two structurally different FRT sites provided a means to clearly distinguish site-specific recombination products from possible artefacts generated by other genomic DNA modifications. Transgenic kanamycin-resistant maize calli were screened for a simple vector integration pattern and GUS activity, to identify NPTII+GUS phenotypes. Callus line #56 containing one 5.5 kb genomic DNA fragment hybridizing to gusA was selected.

Introduction of the FLP Recombinase into Maize Cells.

A suspension culture of line #56 was established. Protoplasts of this line were re-transformed with equimolar amounts of pUbiFLP and pHyg (a vector containing the hpt gene driven by the 35S CaMV promoter). One hundred ninety hygromycin-resistant calli were selected and screened for activation of GUS expression. Most of the hygromycin-resistant re-transformed calli showed GUS activity at the level of 0.063±0.003 nmol MU/min/mg protein (the background GUS activity in line #56 is 0.016±0.006 nmol MU/min/mg protein), while 58 calli showed GUS activity above 0.1 fluorescence unit. Activation of the gusA gene expression should indicate the excisional activity of the FLP protein. These callus lines were not screened for the presence of the FLP protein, thus only about 50% of the hygromycin-resistant calli were expected to express FLP—the average co-transformation efficiency in our system.

Analysis of GUS-Positive Clones.

Several GUS-positive clones were selected to analyze the FLP-mediated excision process. In XhoI-SacI digests of genomic DNA from these clones, the expected 3.2 kb fragment (resulting form excision) hybridizing to the gusA probe was detected. The callus line designated as #122 (derived from line #56) shows only the 3.2 kb band hybridizing to gusA and no DNA sequences hybridizing to the neo probe. The DNA excision reaction in line #122 led to the NPTII-GUS$^+$ phenotype. Protoplasts of line #122 subsequently re-transformed with the neo expression vector regained NPTII activity indicating that the absence of the NPTII activity in line #122 was not related to changes in physiological status Of these cells. PCR analysis further confirmed the presence of the recombination product in genomic DNA of line #122.

Verification or the FLP-Mediated Recombination Reaction.

Although very unlikely, there was a possibility that the neo coding sequence could be removed by a spontaneous recombination process involving the repeated ubiquitin intron sequences 5' of the neo and the gusA coding sequences. Intrachromosomal homologous recombinations could yield a product analogous to the site-specific recombination reaction product. If this was the case, however, the product of recombination would contain the original FRT site positioned in front of the ubiquitin intron sequence, whereas the product formed by FLP-catalyzed site-specific recombination reaction would contain a chimeric FRT that originated from the recombination of the FRT and the FRTm sites. A genomic, DNA fragment amplified by the PCR reaction, consisting of the 5' untranslated sequence of the gusA gene in line #122, Twas subcloned into pGEM7(z) vector and its end containing the FRT site was sequenced. The structure of the integrated FRT site was indeed chimeric and exactly as expected from FLP-mediated site-specific recombination reaction.

Removal of a Selectable Marker.

Transient expression of the FLP gene might provide sufficient FLP protein to recombine FRT sites that were previously integrated into chromatin structures. Accordingly, protoplasts isolated from pUFNeoFmG stably transformed lines were re-transformed with the FLP expression vector (pUbiFLP), and GUS activity was assayed one day after re-transformation. The presence of the GUS activity in extracts from retransformed protoplasts indicated that the recombination reaction took place. This observation also indicated that, providing the transient transformation efficiency is sufficiently high, it is possible to isolate recombination events without additional selection of re-transformed material. To test this, protoplasts were allowed to grow without selection and mini-calli were analyzed for expression of GUS activity. FLP-mediated activation of GUS expression was observed at a frequency of 3–4%. Activation of GUS expression in this experiment was also correlated with the rearrangement of the DNA fragment containing the neo and the gusA genes.

Discussion

The results prove that genomic recombinations can be efficiently induced in maize cells by application of yeast FLP/FRT site-specific recombination system. They occur both when the FLP gene is stably integrated and expressed in maize cells, and under conditions when only transient expression of the FLP gene is provided.

Re-transformation with the FLP-expression vector was used to obtain molecular evidence of site-specific genomic recombination events in maize cells. Approximately one out of four hygromycin-resistant calli showed GUS activity, indicative of the site-specific recombination process. The DNA product of site-specific recombination was identified in all GUS-positive maize cells tested.

EXAMPLE 4

Test of FLP-catalyzed Excisions of Plant Genomic DNA Fragments as a Result of Cross-Pollination of Transgenic *Arabidopsis thaliana* Plants These experiments were conducted to test the feasibility of the FLP/FRT system for transgene excisions in a model plant system (*Arabidopsis thaliana*). These experimental results demonstrate the effectiveness cross-pollination induced site-specific recombination in hybrid plants generated by crossing two parent plants. The recombinase activity can be constitutively expressed in plant organisms with no overall effect on plant growth, and the expression level can be high enough to assure close to 100% excisional efficiency when the recombinase gene is transferred to the another plant by the cross-pollination technique.

PROCEDURES

Vectors

Figure 5A:
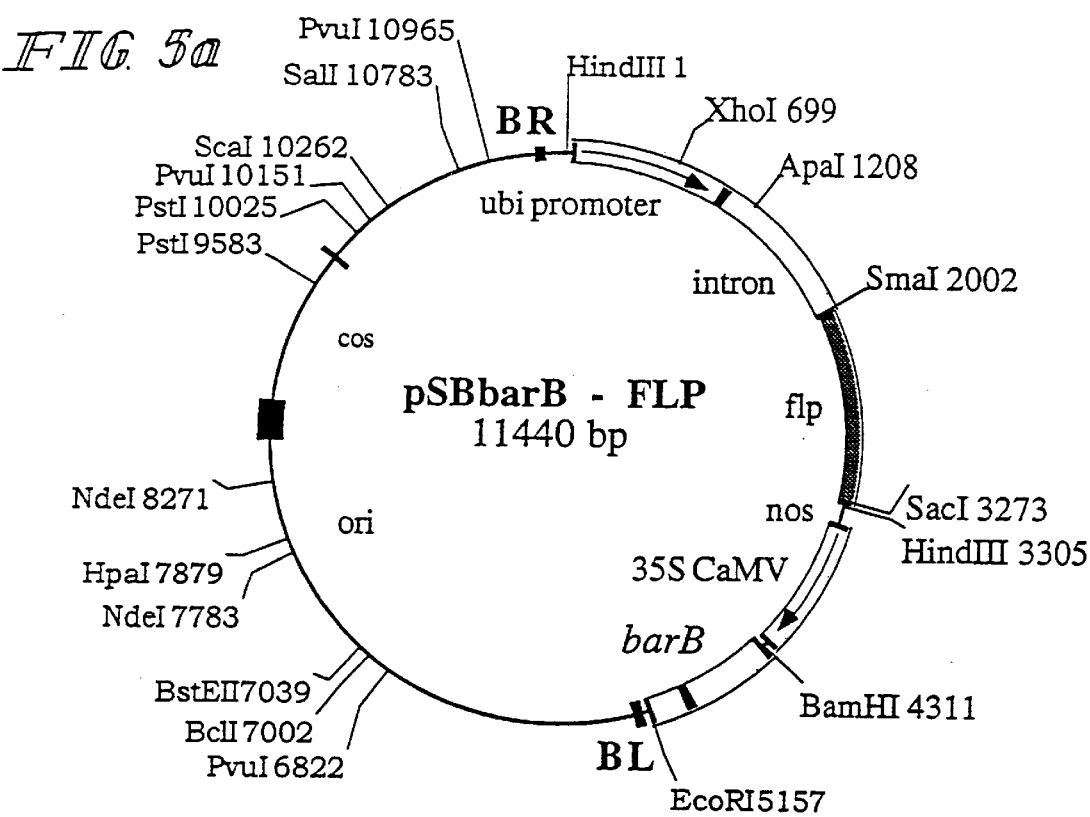
FIG. 5a and FIG. 5b are schematic representations of the Flp-expression vector and FRT-containing expression vector, respectively. These vectors are used to test FLP-mediated excisions of genomic DNA in transgenic Arabidopsis plants.
Figure 5B:
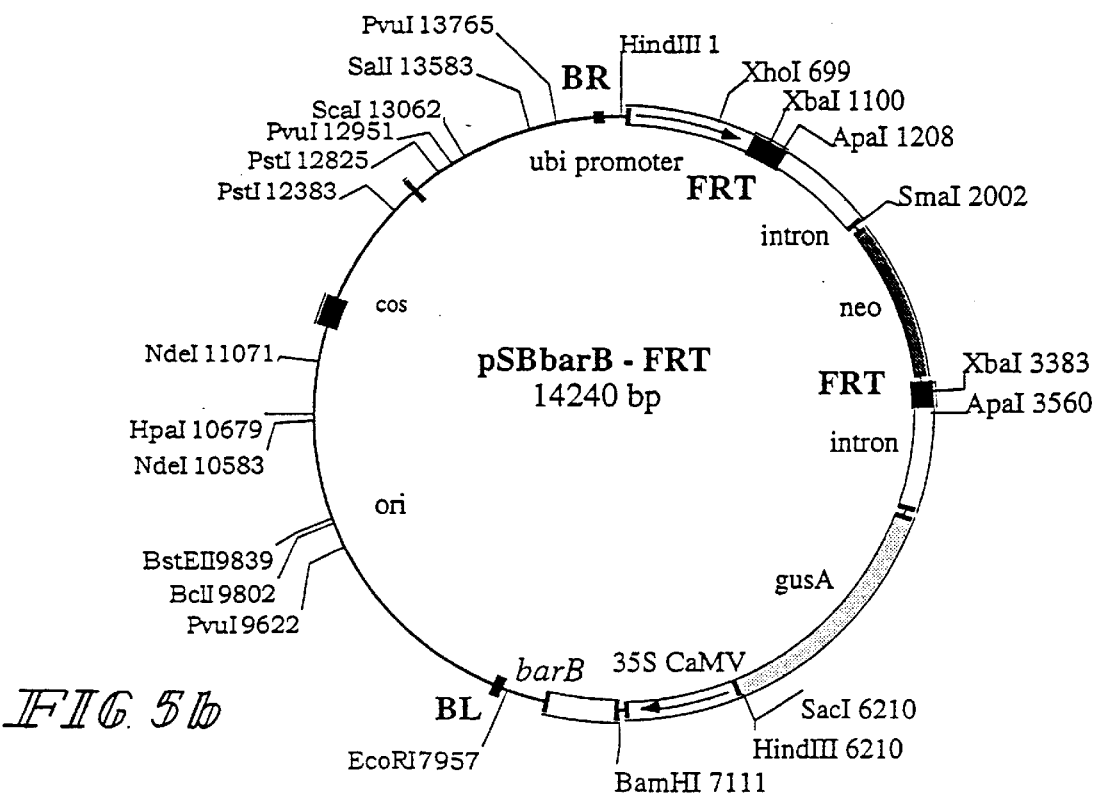

Two pSB11-based Agrobacterium binary vectors (Komari et al., 1996) were Synthesized for transformation of Arabidopsis with chimeric FLP gene and FRT-containing constructions (FIGS. 5a and 5b, respectively). To synthesize the FLP-expression vectors containing the bar gene as a selectable marker (pSBbarB), the HindIII-EcoRI fragment from p35SBarB (Rathore et al., 1993) comprising the bar gene cassette was cloned into respective sites of the pSB11 binary vector. This ligation preserved the HindIII site of the pSB11 for subsequent insertion of the FLP gene, or the FRT-containing inactivated gusA gene.

Plant material

*Arabidopsis thaliana* ecotype Columbia plants were used for transformation experiments. Seeds were sown into plastic pots (3¼×3¼ inch) containing the MetroMix 360 soil mix. After 2 days incubation at 4° C., plants were grown in growth chambers at 24° C., 16 hrs. light/8 hrs. dark photoperiod, and with 60–80% relative humidity. Under such conditions, plants were ready for the vacuum infiltration transformation procedure (Bechtold et al., 1993) in three weeks.

Transformations

A one liter culture of LB medium containing Agrobacterium strains was inoculated two days before transformation. The culture was spun down and bacterial cells resuspended in one liter of infiltration medium (2.2 g MS salts, 50 g sucrose, 1×B5 vitamins, 0.5 g MES, 0.044 μM benzylaminopurine, 200 μl Silwet L-77, pH 5.7). Arabidopsis plants were submerged in the bacterial suspension and a vacuum of 400 mm Hg was drawn. Plants remained under the vacuum for about 5 minutes. After quick release of vacuum, infiltrated plants were covered with plastic wrap and allowed to grow in the growth chamber under conditions described above. After an additional three weeks the seeds were harvested. Primary transformants (T1 plants) containing integrated bar genes were germinated in plastic pots and sprayed with a 0.5% Basta solution. Green plants surviving the herbicide treatment were used for Southern blot analyses to identify simple integration events, and for genetic analysis of bar gene expression in the progeny of transgenic plants.

DNA and RNA Analysis

Southern blot analyses were performed on genomic DNA preparations obtained from 1–2 leaves (about 200 mg fresh weight tissue). Tissue was ground in liquid nitrogen and resuspended in 360 μl of buffer ATL (QIAGEN Inc., Chatsworth, Calif.). Subsequent steps of the DNA isolation procedure were as described in QIAamp Tissue Kit. Twenty five μg of genomic DNA was digested with XhoI, ApaI, and SacI restriction enzymes and the resulting fragments were separated on agarose gels, blotted, and hybridized to gusA, or FLP probes, respectively using standard molecular biology techniques; the probes contained the respective coding sequences of the gusA and FLP genes. Total RNA from leaf tissues of positively identified transgenic plants containing the FLP coding sequences integrated into the genome was isolated (RNeasy Plant total RNA Kit, QIAGEN Inc., Chatsworth, Calif.) for evaluation of the FLP mRNA accumulation. Ten μg total RNA were fractioned on agarose gels in denaturating conditions (7.5% formaldehyde) for the Northern blot analysis.

Cross-Pollination

Flowers were hand pollinated, the flowers selected for pollination contained pistils covered by sepals and petals when the stamens were about half as high as the pistils, yet with anthers green and not shedding pollen. FLP-transformed plants were used as a source of pollen for hand polinating floweres. All lower siliques on the same inflorescence were removed. Three weeks after pollination the seeds were collected and the hybrid progeny seedlings grown.

Staining for GUS Activity

GUS activity in progeny seedlings obtained from the cross-pollination experiments was assayed by histochemical staining with 1 mM 5-bromo-4-chloro-3-indolyl-b-D-glucuronic acid (X-gluc) as described in Jefferson Plant Mol Biol Rep 5:387–405 (1987). Whole seedlings were incubated in 100 μl reaction buffer containing X-gluc at 37° C. overnight. Prior to photography, seedlings were destained in 70% ethanol.

SUMMARY OF RESULTS

Eleven and thirteen primary transformants were selected for FLP-expressing and FRT-containing plants, respectively. Plants surviving selection with Basta were self pollinated to obtain homozygous transgenic FLP-expressing plants and homozygous transgenic FRT-containing plants. Most transgenic plants showed Medelian segregation ratio (3:1) for Basta-resistance in self-pollinated progeny, indicating a single-locus integration of T-DNA segments were frequent in our transformation system. Self-pollination of one T2 generation of Basta-resistant plants produced populations of T3 plants not segregating for Basta-resistance indicating that homozygous T3 plants were obtained. Southern blot analysis of genomic DNA isolated from the identified homozygous T3 plants showed simple vector integration patterns and identification of a single gene integration was possible.

Accordingly, the FLP homozygous plants were selected with a single FLP gene integration. These plants were cross-pollinated to test the efficiency of genomic excisions in the progeny seedlings. Removal of the FRT-flanked DNA segment catalyzed by the FLP protein was monitored by activation of gusA expression in the progeny. Excision of the neo gene operably links the ubi promoter with the gene (see FIGS. 5a and 5b). This was a convenient and reliable monitoring system for testing the activities of site-specific recombination proteins as documented in related studies. All progeny seedlings from a cross between FLP and PRT-containing parents showed GUS activity providing evidence of genomic excisions leading to activation of the gusA gene. This was indicated by hydrolysis of the X-gluc substrate leading to the development of blue color in plant tissues. In contrast, only GUS-negative seedlings were observed in the progeny of selfed parental Arabidopsis plants.

CONCLUSIONS

The observations described in this communication clearly demonstrate that the FLP recombinase expressed in plant tissues can reliably find the FRT sites integrated into genomic DNA and catalyze the excisions of DNA fragments located between them. When FRT sites are integrated into a single locus of the genome, the FLP recombinase-mediated excision approached 100% in the hybrid progeny. In addition these results demonstrate that cross-pollination is an effective method of introducing recombinase activity into a plant to remove sequences flanked by a pair of directly repeated recombination sequences.

We claim:

1. A plant expression vector comprising a tapetum-specific regulatory element of SEQ ID NO: 2, a core promoter, and a structural gene, wherein the expression of the structural gene is regulated by the tapetum-specific regulatory element.

2. The expression vector of claim 1, wherein the structural gene encodes a product that disrupts the function of tapetal cells.

3. The expression vector of claim 2, wherein the nucleic acid sequence encoding the structural gene is flanked by a pair of directly repeated site-specific recombination sequences.

4. The expression vector of claim 3, further comprising a gene encoding a site-specific recombinase that interacts with said directly repeated site-specific recombination sequences, wherein the expression of gene is controlled by an inducible promoter.

5. The expression vector of claim 4, wherein the gene encoding the site-specific recombinase is flanked by said pair of directly repeated site-specific recombination sequences.

6. The expression vector of claim 3, further comprising a gene encoding a eukaryotic selectable marker, wherein said eukaryotic selectable marker gene is flanked by said pair of directly repeated site-specific recombination sequences.

7. The expression vector of claim 3 further comprising nucleic acid sequences that enable replication of the expression vector in a bacterial host, and a gene encoding a bacterial selectable marker.

8. A plant entity, or progeny thereof, consisting essentially of a plant cell, seed or plant produced from the in vitro introduction of the DNA sequence of claim 1 into a plant cell.

9. A plant expression vector comprising a multifunctional DNA sequence; and
   a pair of directly repeated first site-specific recombinase sites flanking the multifunctional DNA sequence; wherein said multifunctional DNA sequence comprises
      a suicide gene;
      a restorer gene, the expression of said suicide gene and said restorer gene each being controlled by an anther-specific regulatory element;
      a pair of directly repeated second site-specific recombination sites flanking the DNA sequence encoding said restorer gene; and
      a gene encoding a second site-specific recombinase that interacts with said directly repeated second site-specific recombination sequences, the expression of the site-specific recombinase gene being controlled by an inducible promoter.

10. A plant entity, or progeny thereof, consisting essentially of a plant cell, seed or plant produced from the in vitro introduction of a DNA construct into a plant cell, said DNA construct comprising a multi-functional DNA sequence flanked by direct repeats of a first site-specific recombination sequence, said multi-functional DNA sequence comprising a suicide gene and a restorer gene, wherein the suicide and restorer genes are each operably linked to an anther-specific promoter, and the restorer gene is flanked by direct repeats of a second site-specific recombination sequence.

11. The plant entity of claim 10 wherein said multi-functional DNA sequence further comprises a second site-specific recombinase gene, wherein the expression of the site-specific recombinase gene is controlled by an inducible promoter.

12. A method for the production of fertile, hybrid plants comprising the steps of
   producing a male fertile transgenic plant by introducing into plant cells a DNA construct comprising a multi-functional DNA sequence and a pair of directly repeated first site-specific recombinase sites flanking the multifunctional DNA sequence wherein said multifunctional DNA sequence comprising a suicide gene, a restorer gene and a pair of directly repeated second site-specific recombination sites flanking the DNA sequence encoding said restorer gene, wherein the expression of said suicide gene and said restorer gene are both controlled by an anther-specific regulatory element;
   producing a male sterile plant by crossing said male fertile transgenic plant, or the progeny of said male fertile transgenic plant with a plant having a DNA sequence comprising a gene encoding the second site-specific recombinase; and
   restoring male fertility by crossing said male sterile plant, or the progeny of said male sterile plant with a plant having a DNA sequence comprising a gene encoding the first site-specific recombinase.

13. A method for the production of fertile, hybrid plants comprising the steps of
   producing a male fertile transgenic plant by introducing into plant cells the vector of claim 9;
   producing a male sterile plant by inducing the expression of the second site-specific recombinase gene in the male fertile transgenic plant, or in the progeny of said male fertile transgenic plant; and
   restoring male fertility by crossing said male sterile plant, or the progeny of said male sterile plant with a plant having a DNA sequence comprising a gene encoding the first site-specific recombinase.

14. A plant entity, or progeny thereof, consisting essentially of a plant cell, seed or plant produced from the in vitro introduction of a DNA sequence into a plant cell, said DNA sequence comprising a tapetum-specific regulatory element of SEQ ID NO: 2, a core promoter, and a structural gene, said structural gene being flanked by a pair of directly repeated site-specific recombination sequences, and the expression of the structural gene is regulated by the tapetum-specific regulatory element.

15. The plant entity of claim 14, or progeny thereof, wherein said structural gene is a suicide gene, wherein the expression of the suicide gene is regulated by the tapetum-specific regulatory element.

16. The plant entity of claim 15, wherein said DNA sequence further comprises a gene encoding a site-specific recombinase that interacts with said directly repeated site-specific recombination sequences, and the expression of the site-specific recombinase gene is controlled by an inducible promoter.

17. A plant expression vector comprising a suicide gene and a restorer gene wherein both the suicide gene and the restorer gene are operably linked to an anther specific promoter, and at least a portion of the nucleic acid sequences encoding said restorer gene and its promoter are flanked by a pair of directly repeated site-specific recombination sequences.

18. A plant entity consisting essentially of a plant cell, seed or plant produced from the in vitro introduction of the DNA sequence of claim 17 into a plant cell.

19. A system for generating male-fertile hybrid plants, said system comprising
   a self fertile plant entity comprising a suicide gene and a restorer gene wherein both the suicide gene and the restorer gene are operably linked to an anther specific promoter, and at least a portion of the nucleic acid sequences encoding said restorer gene and its promoter are flanked by a pair of directly repeated site-specific recombination sequences;
   a male sterility inducing plant entity comprising a gene encoding a site specific recombinase that interacts with said site-specific recombination sequences; and
   a fertility restoration plant entity comprising a restorer gene.

20. The plant entity of claim 18 further comprising a DNA sequence encoding a site-specific recombinase that interacts with said site-specific recombination sequences, wherein the expression of the site-specific recombinase is under the control of an inducible promoter.

21. A system for generating male-fertile hybrid plants, said system comprising
   a male sterile plant entity having a DNA sequence comprising an anther specific promoter operably linked to a suicide gene, said anther specific promoter comprising a 20 base pair nucleotide portion identical in sequence to a consecutive 20 base pair portion of the sequence as set forth in SEQ ID NO: 2, wherein at least a portion of the nucleic acid sequence encoding said anther specific promoter and suicide gene is flanked by a pair of directly repeated site-specific recombination sequences; and
   a fertility restoration plant entity having a DNA sequence comprising a gene encoding a site-specific recombinase that interacts with said site-specific recombination sequences, wherein cross-pollinating the male sterile plant entity with the fertility restoration plant entity produces a male fertile hybrid plant.

22. The system of claim 21 wherein the site-specific recombination sequence is FRT and the site-specific recombinase is FLP.

23. The system of claim 21, wherein the expression of the site-specific recombinase of the fertility restoration plant entity is under the control of an inducible promoter.

24. The hybrid plant, or progeny thereof, produced by crossing the fertility restoration plant entity of claim 21 with the male sterile plant entity of claim 21.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1769 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Oryza sativa
    (B) STRAIN: IR54

(vii) IMMEDIATE SOURCE:
    (B) CLONE: RTS2

(xi) SEQUENCE DESCRIPTION: SEQ ID NO:1:

```
GAGCTCACCG GCGAGGCGGT GCGTCTCCTC GGAGATGTGG TAGAAGCTGG CGCCCCATTT      60

CATGGCGGCG AGCGGGCCGG GCGGCCTCCT GCCGCAGCGG GATTCGGTGG CTAGACCGAT     120

CTGTGGGTGG AGGACGGGGA CGAGGTAGAG GAGACAGAGG CGGCATTGGA AGAGGGGAAG     180

AGGAGGAGGA AGTGGTGGCA GGCAGAGGCG GATGAGGAAC TTGCGCCAGC GACGTGGATA     240

TGGAGGGGGC GACGGCAATG GGGAGGCGGC GATGGAAGCG AGGAGATGGG CAGGCGGCGG     300

AGGCAGCGGT GGATTTTTTT TTTCTTTTTC TTTTTCGGAC CCTTTACCCT GCTCGGTGAT     360

TCTTCTTTTT TATACAGCAC GACGGCTTCT CCTATTCACG ACGCCTCGGC TGGACCATGG     420

ACCGTTGGCC ACTGGAGCAT TCTTCCATGA TCTAGATTTT TTTTTTCACT CAACTTTACT     480

ACTTCACATC TGATGGCTGG TGTTGAATTC ATTGTGCATC CAACGGTCAT TATTAAATTG     540

ATGACGTGGC GCAATGAGGT GACGAAACAC TTTACTTTTT TTACTACTTT AGATCTGTCG     600

GCAGGAGTCC CAGATAGATA CTTGAGCTGG TTAGTTGGGT TTTGGATGGA GTAACTTTCT     660

GCAGACTGCA ACATTCTGAC ACACGTAGCA GCACAAAAGA GTTGCGAACA AACTTGGACT     720

GTTAACATGT CAACGCATAA AACTGAAAAA AAAAACCTGT CAAAATGCAT AATAAATAAA     780

ACTGAAAAAA AATAAGAATA AATGTTGAGA GTGGGATTTG AACCCACGCC CTTTCGGACC     840

AGAACCTTAA TCTGGCGCCT TAGACCAACT CGGCCATCTC AACTTTTTGC TCTGTCATCC     900

AAACAAAGTT ATAAGAAATC ATATAATAAT AACTAAGACT TGATGCCTCA GTAGTTTAGT     960

TAAACTAATT TGAATTTGTT AGTACAGTTT GCATTTCAAA TTGTTCCAAT TTGGACGCCA    1020

CGGCTGGTTT CAGTTGCTCA CGACGCCTCA CACACATATT TTGCTTCCTT GCTTGTGACA    1080

CTAGGGCACA AAACTCCAAC ACTCAAACGA CACTTCACGC ATCTCTCCTG AAATCTTGCA    1140

CCCCCCAACT CTGCATCGTC GCGTATAAAA TGCAGACCAA ACCCCAGCTC AACTCTGCAT    1200

CATCATCATC AACTCGATAG AAAAAGAAAG AAATTAAAAA GAAAATCACG GCGCGTGAGC    1260

TTGCAGAGAC AGCAATGGTG AGAGTTGCTG CCGCCGCGGC GGTGCTCGTG CTGGCGGCGG    1320

CGGCGGCGGC GGCGGCGGCC ATGGCCGCCG AGCCGCCCAC CGATGACGGC GCGGTCCGGG    1380

TGGCGGCGGG GCTGACGAAG TGCGTGTCCG GGTGCGGTAG CAAGGTGACC TCCTGCTTGC    1440

TCGGCTGCTA CGGCGGCGGC GGCGGCGCCG CCGCCGCCGC GACGGCGATG CCGTTCTGCG    1500

TCATCGGCTG CACCAGCGAC GTCTTGTCCT GCGCCACCGG CTGCTCCACC TCGCTCTGAT    1560

TAAGTACTAA TGAAGTAATT AACCGCGCTA ATTAATAATA AATCGCACCT ACGTATGCAC    1620

ATGTGGACTC GCTTGACTAA TTAAATACTG CCATGCGAAT GCGATTAGTG GATTATGAAA    1680

AGAGGAAATG TAAGAACTCA TGGCTCTCTC TGTGCCATGC CTGTACTGCA TTGAAATGAA    1740

TCTGCATGCA GCCATGAACT GATATACAA                                     1769
```

(2) INFORMATION FOR SEQ ID NO:2:

(i) SEQUENCE CHARACTERISTICS:
        (A) LENGTH: 1278 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

```
GAGCTCACCG GCGAGGCGGT GCGTCTCCTC GGAGATGTGG TAGAAGCTGG CGCCCCATTT      60

CATGGCGGCG AGCGGGCCGG GCGGCCTCCT GCCGCAGCGG GATTCGGTGG CTAGACCGAT     120

CTGTGGGTGG AGGACGGGGA CGAGGTAGTG GAGACAGAGG CGGCATTGGA AGAGGGGAAG     180

AGGAGGAGGA AGTGGTGGCA GGCAGAGGCG GATGAGGAAC TTGCGCCAGC GACGTGGATA     240

TGGAGGGGGC GACGGCAATG GGGAGGCGGC GATGGAAGCG AGGAGATGGG CAGGCGGCGG     300

AGGCAGCGGT GGATTTTTTT TTTCTTTTTC TTTTTCGGAC CCTTTCACCT GCTCGGTGAT     360

TCTTCTTTTT TATACAGCAC GACGGCTTCT CCTATTCACG ACGCCTCGGC TGGACCATGG     420

ACCGTTGGCC ACTGGAGCAT TCTTCCATGA TCTAGATTTT TTTTTTCACT CAACTTTACT     480

ACTTCACATC TGATGGCTGG TGTTGAATTC ATTGTGCATC CAACGGTCAT TATTAAATTG     540

ATGACGTGGC GCAATGAGGT GACGAAACAC TTTACTTTTT TTACTACTTT AGATCTGTCG     600

GCAGGAGTCC CAGATATGTA TACTTGAGCT GGATTAGTTG GGTTTTGGAT GGAGTAACTT     660

TCTGCAGACT GCAACATTCT GACACACGTA GCAGCACAAA AGAGTTGCGA ACAAACTTGG     720

ACTGTTAACA TGTCAACGCA TAAAACTGAA AAAAAAAACC TGTCAAAATG CATAATAAAT     780

AAAACTGAAA AAAAATAAGA ATAAATGTTG AGAGTGGGAT TTGAACCCAC GCCCTTTCGG     840

ACCAGAACCT TAATCTGGCG CCTTAGACCA ACTCGGCCAT CTCAACTTTT TGCTCTGTCA     900

TCCAAACAAA GTTATAAGAA ATCATATAAT AATAACTAAG ACTTGATGCC TCAGTAGTTT     960

AGTTAAACTA ATTTGAATTT GTTAGTACAG TTTGCATTTC AAATTGTTCC AATTTGGACG    1020

CCACGGCTGG TTTCAGTTGC TCACGACGCC TCACACACAT ATTTTGCTTC CTTGCTTGTG    1080

ACACTAGGGC ACAAAACTCC AACACTCAAA CGACACTTCA CGCATCTCTC CTGAAATCTT    1140

GCACCCCCCA ACTCTGCATC GTCGCGTATA AAATGCAGAC CAAACCCCAG CTCAACTCTG    1200

CATCATCATC ATCAACTCGA TAGAAAAAGA AAGAAATTAA AAAGAAAATC ACGGCGCGTG    1260

AGCTTGCAGA GACAGCAA                                                  1278
```

(2) INFORMATION FOR SEQ ID NO:3:

(i) SEQUENCE CHARACTERISTICS:
         (A) LENGTH: 16 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

```
CCCCAACCTC GTGTTG                                                      16
```

(2) INFORMATION FOR SEQ ID NO:4:

(i) SEQUENCE CHARACTERISTICS:
         (A) LENGTH: 19 base pairs
         (B) TYPE: nucleic acid
         (C) STRANDEDNESS: single

```
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

CGCGATCCAG ACTGAATGC                                                         19
```